United States Patent [19]

Armstrong et al.

[11] Patent Number: 4,497,899
[45] Date of Patent: Feb. 5, 1985

[54] IMMUNOASSAY FOR *CHLAMYDIA TRACHOMATIS* ANTIGENS

[75] Inventors: Alan S. Armstrong, Waukegan; John E. Herrmann, Hawthorn Woods; Lawrence V. Howard, Vernon Hills, all of Ill.

[73] Assignee: Abbott Laboratories, North Chicago, Ill.

[21] Appl. No.: 479,414

[22] Filed: Mar. 28, 1983

Related U.S. Application Data

[63] Continuation-in-part of Ser. No. 367,697, Apr. 12, 1982, abandoned.

[51] Int. Cl.$^3$ .................... G01N 33/54; G01N 33/56
[52] U.S. Cl. .................................. 436/510; 436/518; 436/534; 436/543; 436/804; 436/811; 436/815; 436/823; 436/825; 436/826; 435/4; 435/7; 435/259
[58] Field of Search ............... 436/510, 518-534, 436/543-547, 804, 811, 823, 824, 815, 825, 826; 435/4, 7, 14, 21, 25, 259

[56] References Cited

U.S. PATENT DOCUMENTS

| | | | |
|---|---|---|---|
| 4,067,959 | 1/1978 | Bolz | 424/1 |
| 4,118,469 | 10/1978 | Caldwell et al. | 424/1 |
| 4,188,371 | 2/1980 | Weetall | 424/1 |
| 4,241,045 | 12/1980 | Gaafar | 424/1 |
| 4,254,082 | 3/1981 | Schick et al. | 422/55 |
| 4,427,782 | 1/1984 | Caldwell et al. | 436/542 |

FOREIGN PATENT DOCUMENTS

| | | |
|---|---|---|
| 17460 | 3/1980 | European Pat. Off. |
| 2047889 | 3/1980 | United Kingdom |

OTHER PUBLICATIONS

Caldwell, H. D. et al., Infection and Immunity, vol. 31(3), pp. 1161–1176 (3–1981).
Terho, P. et al., J. of Medical Microbiology, vol. 14(1), pp. 77–87 (1981).
Howard, L. V., Infection and Immunity, vol. 11(4), pp. 698–703 (1975).
Hermann, J. E. et al., Abstract Annual Meetings Amer. Society for Microbiology, vol. 84, Abstract C250 (1984).
*The Journal of Infectious Diseases*, vol. 121, No. 1, Jan. 1970, pp. 1–9, Collins, A. R. et al.
*JAMA*, May 1, 1981, vol. 245, No. 17, "The Chlamydia Epidemic" Holmes, King K., pp. 1718–1723.
*Journal of Immunoassay*, 2 (3 and 4), 239–262 (1981), "Detection of Chlamydia Trachomatis Antigen by Radioimmunoassay" Terho et al.

*Primary Examiner*—Ben R. Padgett
*Assistant Examiner*—M. Moskowitz
*Attorney, Agent, or Firm*—James L. Wilcox

[57] ABSTRACT

The present disclosure relates to a solid phase immunoassay for the detection of *Chlamydia trachomatis* antigens in a clinical specimen, wherein the *Chlamydia trachomatis* antigens to be determined are coated or adsorbed on the solid phase.

14 Claims, No Drawings

IMMUNOASSAY FOR *CHLAMYDIA TRACHOMATIS* ANTIGENS

This application is a continuation-in-part of U.S. Ser. No. 367,697, filed Apr. 12, 1982, now abandoned.

The present invention relates to an immunoassay procedure for the detection of *Chlamydia trachomatis* antigen in a clinical specimen. In particular, the present invention relates to a solid phase immunoassay wherein the *Chlamydia trachomatis* antigen to be determined is coated directly on the solid phase.

It has been reported that the incidence of chlamydial infection has dramatically increased and has approached if not exceeded the levels reported for gonorrheal infection. Currently accepted procedures for the detection of chlamydial infection rely upon culture techniques. However, culture procedures are laborious, time-consuming, expensive, and subject to technician error due to the extensive amount of handling involved.

In addition to culture procedures, various immunoassay techniques for the detection of chlamydial infection have been described. U.S. Pat. No. 4,118,469 describes the use of an antigen, common to all strains of *Chlamydia trachomatis* organisms, to detect antibody of *Chlamydia trachomatis* in sera using counterimmunoelectrophoresis techniques. Great Britain patent application Ser. No. 2,047,889A discloses a serological test for *Chlamydia trachomatis* antibodies employing a microimmunofluorescence procedure utilizing a formaldehyde stabilized antigen. European Patent Application 17460 describes a microimmunofluorescence procedure for detecting antibodies to *Chlamydia trachomatis* using a reticulated body antigen. As noted these procedures are limited to the detection of antibodies to *Chlamydia trachomatis*. False-positive or false-negative results may be obtained when antibodies to *Chlamydia trachomatis* rather than *Chlamydia trachomatis* antigens are detected because antibodies are produced only in response to an infectious agent, i.e., an antigen, in the body and antibodies often remain long after the disease has been cured. Therefore, in order to accurately diagnose the presence of chlamydial infection, it is preferred to assay for antigens rather than antibodies.

Therefore, it is an object of the present invention to provide a solid phase immunoassay procedure for the detection of *Chlamydia trachomatis* antigens having the accuracy of the culture techniques but eliminiating the disadvantages associated with the known immunoassay and culture procedures.

The present invention relates to an immunoassay for determining *Chlamydia trachomatis* antigen in a clinical specimen comprising:

(a) lysing *Chlamydia trachomatis* cells in the specimen to release *Chlamydia trachomatis* antigen;

(b) coating a solid support with *Chlamydia trachomatis* antigen in the specimen;

(c) treating the antigen coated solid support with chlamydial antibody to form an antigen-chlamydial antibody complex on the solid support;

(d) treating the antigen-chlamydial antibody complex with antiglobulin; and (e) determining the antiglobulin bound to the antigen-chlamydial antibody complex as a measure of the *Chlamydia trachomatis* antigen in the specimen.

The present invention further relates to an immunoassay for determining *Chlamydia trachomatis* antigen in a clinical specimen wherein the *Chlamydia trachomatis* antigen is coated on a bare solid support.

In accordance with the methods of the present invention, a clinical specimen is obtained from a patient suspected of having chlamydial infection utilizing conventional medical and microbiological techniques. Such clinical specimens include, for example, swab specimens obtained from the cervix, urethra, throat or anus of a patient and body fluids such as synovial fluid or fluid from lesions. The clinical specimens thus obtained consists of chlamydial bacteria organisms containing the *Chlamydia trachomatis* antigen to be determined. In order to increase the sensitivity of the assay, it is preferred to lyse the organisms to release the *Chlamydia trachomatis* antigens thereby increasing the number of antigenic sites available for binding to chlamydial antibody. Conventional techniques that may be employed to lyse the bacteria in order to release antigens include, for example, the use of solvent dilution or high pH lysing solution, heating, enzyme treatment, and physical agitation, such as sonication and centrifugation. In a preferred embodiment of the present invention, the swab specimen is placed into a suitable lysing medium. Illustrative of suitable lysing media include, for example, phosphate buffered saline, saline and water. It is preferred to employ phosphate buffered saline. The submerged swab is rapidly twisted back and forth for about fifteen seconds or agitated in order to release *Chlamydia trachomatis* antigens into the medium. It has unexpectedly been found that the addition of a surfactant such as Triton X-100, Tween-80, dodecylsulfate salts, deoxycholate salts or other bile salts to the lysing medium increases the sensitivity of the method of the present invention. It has been found that the addition of deoxycholate salts, preferably chenodeoxycholate, to the lysing medium produces superior sensitivity and specificity with respect to the results obtained employing the method of the present invention. In addition to a surfactant, a reducing agent such as, for example, dithiothreitol, 2-mercaptoethanol, N-acetyl-cystine and the like is preferably added to the lysing medium.

According to the preferred embodiment of the present invention, the medium containing the *Chlamydia trachomatis* antigen to be assayed is contacted with a bare solid support. The term "bare solid support" refers to a solid support that is untreated or uncoated with either proteins or antibody specific for *Chlamydia trachomatis*. That is, there is no chemical or immunological binding between the *Chlamydia trachomatis* antigen to be determined and any substance that may be found on the solid support. The medium containing the *Chlamydia trachomatis* antigen and the solid support is incubated for a sufficient period of time to permit the *Chlamydia trachomatis* antigen to "coat" or "adsorb" onto the solid support. Following the incubation period, the antigen coated solid support is washed with water or buffer to remove unadsorbed bacteria and tissue debris. The antigen coated solid support is brought in contact with a chlamydial antibody. The resulting mixture is incubated for a period of time sufficient to allow the formation of an antigen-chlamydial antibody complex on the solid support. The complex on the solid support is washed with water or buffer to remove unbound chlamydial antibody and is treated with antiglobulin. The resulting mixture is incubated for a period of time sufficient to allow the formation of an antigen-chlamydial antibody-antiglobulin complex on the solid support. The complex thus formed is washed with water or buffer to remove unbound antiglobulin and the amount of antiglobulin bound to antigenchlamydial antibody complex is determined as a measure of the *Chlamydia trachomatis* antigen in the sample.

Solid support refers to an insoluble polymeric material sorptive for the antigen. Known materials of this type include hydrocarbon polymers such as polystyrene, polypropylene, polybutylene, butyl rubber and other synthetic rubbers. Other suitable organic polymers include silastic rubber, polyesters, polyamides, cellulose and cellulosic derivatives, polymers of acrylates, polymers of methacrylates, and polymers of vinly chloride such as polyvinylchloride. Copolymers such as graft copolymers of polystyrene are also useful. In addition to the foregoing materials, the solid support surface may comprise silica gel, silicone wafers, glass insoluble protein metals and the solid support may be in the form of beads, tubes, strips, disks, microtitration plates and the like.

The term "chlamydial antibody" refers to an antibody that is "immunoreactive" with one or more strains of *Chlamydia trachomatis* antigens, and is raised in a human or nonhuman species such as rabbit, goat, horse, sheep, guinea pig, etc. The chlamydial antibodies effective in the methods of the present invention are produced employing an antigen common to the prevalent strains of *Chlamydia trachomatis*, as an immunogen in accordance with known techniques. Such antigens are readily ascertained by one of ordinary skill in the art and include for example, *Chlamydia trachomatis* LGV Type II strain T'ang, *Chlamydia trachomatis* Trachoma serotype A strain HAR-13, *Chlamydia trachomatis* LGV Type II strain 434 and the like. Although a single antigen may be utilized to produce chlamydial antibody, a "pool" of antigens from various strains may be employed in the serial immunization of an animal, to produce a chalmydial antibody. In addition, monoclonal antibody to *Chlamydia trachomatis* may be employed as the chalmydial antibody.

The term "antiglobulin" refers to an antibody specific for a species for which the chlamydial antibody was derived and is raised in a nonhuman species such as rabbit, goat, horse, sheep, guinea pig, etc. The antiglobulin bound to the antigen-chlamydial antibody may be determined as a measure of the *Chlamydia trachomatis* antigen in the sample. The antiglobulin may be directly labeled by conventional fluorescent dyes, enzymes or radioactive labels to permit determination of the amount bound, or it may be indirectly labeled by further reaction, for example, with fluorescent dyes, enzymes or radioactive labels by conventional methods.

It is preferred to employ antiglobulin directly labeled with an enzyme. Examples of enzymes include catalase, peroxidase, urease, gluocose oxidase, phosphatase, and the like. If direct labeling of the antiglobulin is employed, following the addition of labeled antibody and formation of the labeled complex, an enzyme substrate is added to the liquid and/or solid phase of the reaction mixture and an enzyme determination is performed by conventional colorimetric, fluorometric, or spectrophotometric techniques. In the case of indirect labeling, that is, the antiglobulin is unlabeled, the complex formed upon addition of the unlabeled antiglobulin is washed to remove unbound antiglobulin and is subsequently reacted with a labeled antibody to the antiglobulin and the labeled antibody is then measured.

For the purpose of giving those skilled in the art, a better understanding of the present invention, the following illustrative, nonlimiting examples are given. The chlamydial antibody employed in the Examples was produced using *Chlamydia trachomatis* LGV-type II strain 434.

EXAMPLE I

1. A urogenital swab sample is placed into a tube containing 1 ml of phosphate buffered saline (pH 7.2) with 0.1% sodium doeycholate and 1:10,000 thimerosal. After five minutes, the submerged swab is rapidly twisted back and fourth for about fifteen seconds or agitated thereby releasing *Chlamydia trachomatis* antigen into the buffered solution. The swab is then rotated against the inner edge of the tube.

2. A 200 μl aliquot of the buffered solution containing the *Chlamydia trachomatis* antigen is added to appropriate wells of the reaction tray containing a plastic bead and is covered and incubated at 37° C. for thirty minutes.

3. The plastic bead is washed with water to remove unadsorbed bacteria and tissue debris.

4. To the wells containing the washed beads is added 200 μl of a solution containing 10 μg/ml of rabbit chlamydial antibody in 100% normal human serum to which 0.1% Tween-20, 0.005M ethylenediaminotetraacetic acid and 1:10,000 thimerosal had been added.

5. The reaction trays are covered and incubated for about one hour at 37° C.

6. Following this second incubation, unbound chlamydial antibody is removed from the wells and the beads are washed with water.

7. To the wells containing the washed beads is added 200 μl of a solution containing 1 μg/ml of antibody to rabbitt IgG covalently linked to horseradish peroxidase, 45% fetal calf serum, 0.15% Tween-20, 5% normal human serum 0.005M ethylenediaminotetraacetic acid and 1:10,000 thimerosal in 0.05M Tris buffer (pH 7.2).

8. The reaction trays are covered and incubated for about one hour at 37° C.

9. Following the incubation, unbound antibody to rabbit IgG-horseradish peroxidase is removed and the beads are washed with water.

10. The beads are transferred to assay tubes to which is added 300 μl of a freshly prepared substrate solution containing approximately 27 mg of o-phenylenediamine 2 HCl in 5 ml in citrate-phosphate buffer (pH 5.5) containing 0.02% hydrogen peroxide and 0.01% thimerosal. The tubes are incubated for ten minutes at room temperature.

11. Following the incubation, 2 ml of 1N hydrochloric acid are added to each tube.

12. The appearance of a yellow color in the tube, qualitatively indicated the presence of *Chlamydia trachomatis* antigen in the sample.

13. The absorbance of the resulting solutions were measured at 492 nm using a spectrophotometer. The intensity of color is proportional to the quantity of *Chlamydia trachomatis* antigens originally present in the sample.

EXAMPLE II

Laboratory strains of *Chlamydia trachomatis*, originally isolated from patients with chlamydial infections and representative of genital *C. trachomatis* strains, were titrated in McCoy cells to determine the number of inclusion-forming units. Dilutions of the suspension were prepared so as to contain approximately 50 inclusion-forming units per test (in phosphate buffered saline containing 0.1% sodium deoxycholate and 1:10,000 thimerosal) and assayed by the procedure described in Example I (Steps 2-10). The results obtained are represented in Tables I and II and illustrate the sensitivity of the assay with respect to *Chlamydia trachomatis* antigens. A positive test for *Chlamydia trachomatis* in Table I-III is indicated by an absorbance ($A$492) value greater than or equal to 0.05 plus the absorbance value of the background (negative control). As used herein the term "IFU" refers to inclusion forming units/200 μL in the sample.

TABLE I

| *Chlamydia trachomatis* Serotype | IFU | $A492^a$ | Detection Of *Chlamydia trachomatis* Antigens |
| --- | --- | --- | --- |
| E | 15 | 0.18 | Positive |
| G | 18 | 0.44 | Positive |
| J | 22 | 0.53 | Positive |
| K | 64 | 0.42 | Positive |
| Negative Control | — | 0.04 | — |

$^aA492 \geq 0.09$ is positive

TABLE II

| *Chlamydia trachomatis* Serotype | IFU | $A492^b$ | Detection Of *Chlamydia trachomatis* Antigens |
| --- | --- | --- | --- |
| D | 72 | 0.31 | Positive |
| F | 80 | 0.19 | Positive |
| H | 250 | 0.28 | Positive |
| H | 100 | 0.14 | Positive |
| I | 92 | 0.40 | Positive |
| Negative Control | — | 0.06 | — |

$^bA492 \geq 0.11$ is positive

Dilutions of the suspensions were also prepared in phosphate-buffered saline containing 0.1% chenodeoxycholate, 0.01M dithiothreitol and 1:10,000 thimerosal and assayed by the procedure described in Example I (steps 2-10). The results obtained are represented in Table III and illustrate the sensitivity of the assay with respect to *Chlamydia trachomatis* antigens.

TABLE III

| *Chlamydia trachomatis* Serotype | IFU | $A492^a$ | Detection Of *Chlamydia trachomatis* Antigens |
| --- | --- | --- | --- |
| D | 72 | 0.46 | Positive |
| F | 80 | 0.31 | Positive |
| H | 250 | 0.54 | Positive |
| H | 100 | 0.24 | Positive |
| I | 92 | 0.50 | Positive |
| Negative Control | — | 0.10 | — |

$^cA492 \geq 0.15$ is positive

As evidenced by the above Example, the methods of the present invention provide a solid phase immunoassay for *Chlamydia trachomatis* antigens. As evidenced in Table III, the use of chenodeoxycholate as a surfactant to lyse the organism contains the *Chlamydia trachomatis* antigens significantly increases the sensitivity of the assay. In addition, the methods described are effective in detecting *Chlamydia trachomatis* in clinical specimens. The method of the present invention minimizes sample handling and possesses the ability to detect both live and dead organisms. In addition, qualitative as well as quantitative results may be obtained.

Another embodiment of the present invention relates to the use of a labeled chlamydial antibody in lieu of the previously described chlamydial antibody and antiglobulin. A "labeled chlamydial antibody" refers to a chlamydial antibody that is directly labeled in accordance with known techniques by conventional fluorescent dyes, enzymes or radioactive labels. If a labeled chlamydial antibody is utilized, it is preferred to employ chlamydial antibody directly labeled with an enzyme. Examples of enzymes include catalase, peroxidase, urease, glucose oxidase, phosphatase, and the like. A labeled chlamydial antibody may be utilized in the methods of the present invention in accordance with the following procedure. The medium containing the *Chlamydia trachomatis* antigen to be assayed is contacted with a solid support and is incubated for a sufficient period of time to permit an effective amount of the antigen to coat onto the solid support. Following the incubation period, the antigen coated solid support is washed with water or buffer to remove unadsorbed bacteria and tissue debris. The antigen coated solid support is brought in contact with labeled chlamydial antibody. The resulting mixture is incubated for a sufficient period of time to allow formation of antigen-labeled chlamydial antibody complex on the solid support. The antigen-labeled chlamydial antibody complex on the solid support is washed with water or buffer to remove unbound labeled chlamydial antibody. The amount of labeled chlamydial antibody bound to the antigen complex is determined as a measure of the *Chlamydia trachomatis* antigen in the sample.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included therein.

What is claimed is:

1. A method for determining *Chlamydia trachomatis* antigen in a clinical specimen comprising:
    (a) lysing *Chlamydia trachomatis* cells in the specimen to release *Chlamydia trachomatis* antigen;
    (b) coating a bare solid support with *Chlamydia trachomatis* antigen in the specimen;
    (c) separating the antigen coated solid support from the specimen;
    (d) treating the antigen coated solid support with chlamydial antibody to form an antigen-chlamydial antibody complex on the solid support;
    (e) separating the antigen-chlamydial antibody complex from unbound chlamydial antibody;
    (f) treating the antigen-chlamydial antibody complex with a labeled antiglobulin to form an antigen-chlamydial antibody-labeled antiglobulin complex on the solid support;
    (g) separating the antigen-chlamydial antibody-labeled antiglobulin complex from unbound labeled antiglobulin; and
    (h) determining the labeled antiglobulin bound to the antigen-chlamydial antibody complex as a measure of the *Chlamydia trachomatis* antigen in the specimen.

2. A method according to claim 1 wherein the *Chlamydia trachomatis* antigen is lysed using buffered saline solution and a surfactant.

3. A method according to claim 2 wherein the surfactant is a deoxycholate salt.

4. A method according to claim 3 wherein the deoxycholate salt is chenodeoxycholate.

5. A method according to claim 4 wherein a reducing agent is added to the buffered saline solution and the surfactant.

6. A method according to claim 5 wherein the reducing agent is dithiothreitol and the surfactant is chenodeoxycholate.

7. A method according to claim 1 wherein the antiglobulin is labeled with an enzyme.

8. A method for determining *Chlamydia trachomatis* antigen in a clinical specimen comprising:
   (a) lysing *Chlamydia trachomatis* cells in the specimen to release *Chlamydia trachomatis* antigen;
   (b) coating a bare solid support with the lysed *Chlamydia trachomatis* antigen;
   (c) separating the antigen coated solid support from the specimen;
   (d) treating the antigen coated solid support with chlamydial antibody to form an antigen-chlamydial antibody complex on the solid support;
   (e) separating the antigen-chlamydial antibody complex from unbound chlamydial antibody;
   (f) treating the antigen-chlamydial antibody complex with antiglobulin, to form an antigen-chlamydial antibody-antiglobulin complex on the solid support;
   (g) separating the antigen-chlamydial antibody-antiglobulin complex from unbound antiglobulin;
   (h) treating the antigen-chlamydial antibody-antiglobulin complex with labeled antibody to the antiglobulin to form an antigen-chlamydial antibody antiglobulin-labeled antibody complex on the solid support;
   (i) separating the antigen-chlamydial antibody-antiglobulin-labeled antibody complex from unbound labeled antibody; and
   (j) determining the labeled antibody bound to the antigen-chlamydial antibody-antiglobulin complex as a measure of the *Chlamydia trachomatis* antigen in the specimen.

9. A method according to claim 8 wherein the *Chlamydia trachomatis* antigen is lysed from the specimen using a buffered saline solution and a surfactant.

10. A method according to claim 9 wherein the surfactant is a deoxycholate salt.

11. A method according to claim 10 wherein a reducing agent is added to the buffered saline solution and the surfactant.

12. A method accoring to claim 11 wherein the reducing agent is dithiothreitol and the surfactant is chenodeoxycholate.

13. A method according to claim 8 wherein the antiglobulin is labeled with an enzyme.

14. A method for determining *Chlamydia trachomatis* antigen in a clinical specimen comprising:
   (a) lysing the *Chlamydia trachomatis* antigen;
   (b) coating a bare solid support with the lysed *Chlamydia trachomatis* antigen;
   (c) separating the antigen coated solid support from the specimen;
   (d) treating the antigen coated solid support with labeled chlamydial antibody;
   (e) separating the antigen coated solid support with the labeled chlamydial antibody from unbound labeled chlamydial antibody; and
   (f) determining the labeled chlamydial antibody bound to the antigen coated solid support as a measure of the *Chlamydia trachomatis* antigen in the specimen.

* * * * *